United States Patent [19]

Rao et al.

[11] 3,994,783

[45] Nov. 30, 1976

[54] DIFFERENTIAL ASSAY OF CREATINE PHOSPHOKINASE ISOENZYMES

[75] Inventors: Parinam Srinivasa Rao, Shrewsbury; James J. Lukes, Worcester; Hiltrud S. Mueller, Framingham, all of Mass.

[73] Assignee: Calbiochem, La Jolla, Calif.

[22] Filed: Sept. 26, 1975

[21] Appl. No.: 616,933

[52] U.S. Cl. ............................................ 195/103.5 R
[51] Int. Cl.² ........................................... C12K 1/04
[58] Field of Search ............................... 195/103.5 R

[56] References Cited
UNITED STATES PATENTS
3,540,984  11/1970  Deutsch ..................... 195/103.5 R

OTHER PUBLICATIONS

Warren, "Activation of Serum Creative Kinase by Dithiothreitol", Clinical Chem., vol. 18, No. 5, 1972, pp. 473–475.

Roe et al., "Combined Isoenzyme Analysis in the Diagnosis of Myocardial Injury: Application of Electrophoretic Methods for the Detection and Quantitative of the Creative Phosphokinase MB Isoenzyme", J. of Laboratory and Clinical Medicine, 80, (1972), pp. 577–590.

*Primary Examiner*—A. Louis Monacell
*Assistant Examiner*—C. A. Fan
*Attorney, Agent, or Firm*—Delmar H. Larsen

[57] ABSTRACT

A process for the determination of creatine phosphokinase MB-isoenzyme (CPK-MB) level in serum in which CPK is determined before and after MB-activation with 1,4-dimercapto-2,3-dihydroxy butane or 2-mercaptoethanol, preferably in an assay system using the ATP/ADP conversion. The difference in the two values found is due to the CPK-MB present. The invention is of particular utility in the diagnosis and treatment of myocardial damage.

9 Claims, No Drawings

DIFFERENTIAL ASSAY OF CREATINE PHOSPHOKINASE ISOENZYMES

This invention relates to an improved method for determining the level of the isoenzymes of creatine phosphokinase in serum, and more particularly to a procedure for determining the isoenzyme especially critical in the diagnosis of myocardial infarction.

In clinical practice, the determination of the activity of various serum enzymes is of great usefulness in diagnosis and treatment. A summary review appears on pages 584–600 of *The Geigy Scientific Tables*, 7th Edition, Ardsley and Basel, (1970), and on pages 125–148 of the text *Clinical Chemistry* by R. Richterich, Basel and New York (1969), which are both hereby incorporated herein by reference together with the articles cited therein.

A determination of creatine phosphokinase is of importance in diagnosing cardiac and muscular ailments. A number of assay methods for this are available, several of which are referenced in the Geigy text just cited, and in pages 310–313 of the Richterich text just cited. In recent years it has been realized that creatine phosphokinase (CPK) exists in the form of at least three isoenzymes, designated CPK-MM, CPK-MB, and CPK-BB. A useful summary is given in an article by Roberts et al., in *The American Journal of Cardiology* 33 pages 650–654, (1974), and by Roe et al., *Journal of Laboratory and Clinical Medicine* 80, pages 577–590 (1972). These articles together with the papers cited therein are hereby incorporated herein by reference.

Recent literature, for example, the Roberts et al., article already cited hereinabove, makes it clear that undifferentiated CPK activity in serum is not definitive for myocardial injury, but rather it is necessary to determine the level of CPK-MB.

The standard methods of CPK determination as cited for example, in the Geigy and Richterich texts referred to above, do not differentiate among the several isoenzymes. Each one gives a value for "CPK" which in fact may be CPK-MM alone or variously combined with the other two enzymes present. In order to determine CPK-MB by itself, recourse has heretofore been had to relatively complicated and timeconsuming procedures. For example, in the Roberts et al., article cited above, the isoenzymes were separated by cellulose acetate electrophoresis, the isoenzymes recovered from portions of the cellulose acetate strips, and then determined by a fluorescent method. In the Roe et al., paper, a somewhat similar procedure was followed, using agar gel electrophoresis followed by a fluorometric assay.

An object of the present invention is to provide a method for determining CPK-MB in serum by a rapid, simple, and direct procedure.

Other objects of the invention will appear as the description thereof proceeds.

Generally speaking, and in accordance with illustrative embodiments of the invention, we determine the concentration of the CPK-MB isoenzyme in a test fluid such as serum by separately determining the CPK activity after first having activated the CPK present by the addition of the fluid prior to the activity determination of an activating thiol other than 1,4-dimercapto-2,3-dihydroxy butane and mercaptoethanol and then carrying out a similar determination in which prior to the CPK activity testing a CPK-MB activator selected from the class consisting of 1,4-dimercapto-2,3dihydroxy butane and mercaptoethanol and mixtures thereof is added. In the first instance the CPK-MM isoenzyme is responsible for the activity value obtained, whereas in the second, both the CPK-MM and CPK-MB isoenzymes contribute to the activity value determined. Accordingly, the arithmetic difference between the activities obtained is a direct measure of the CPK-MB level sought. Otherwise stated, the increase in observed activity from the first to the second sub-procedure is due to the CPK-MB isoenzyme, and provides the value sought.

The activity determination in both sub-procedures is carried out by determining the enzymatic activity of the CPK in catalyzing the ATP/ADP conversion.

As is well known, the important biochemical conversion:

$$\text{Creatine} + \text{ATP} \rightleftharpoons \text{creatine phosphate} + \text{ADP} \qquad [1]$$

is reversibly catalyzed by CPK in such a fashion that the "forward" reaction in which ATP is converted to ADP is favored at pH 9, while the reverse reaction, in which ADP is transformed to ATP, is favored at pH 7. The reaction from right to left, that is, the so-called reverse reaction, is about 10 times faster than the forward reaction so that the former is in general preferred and is more widely used. Our invention, however, is applicable to both, and indeed to the various procedures which appear in the literature, many of which are cited in the Richterich test already noted. Details of our preferred assay will appear later hereinbelow.

CPK becomes inactivated by storage of serum or plasma even for a relatively short time, so that it is common good practice to CPK assays to reactivate the CPK by adding a thiol, for which any of those to be mentioned are suitable.

Of the first class of activators set forth above, cysteine, glutathione, mercaptoacetic acid, thiodiglycolic acid, 2-aminoethylisothiouronium bromide, and others may be used. We prefer to use glutathione.

The activators of the second class comprise the three isomers of 1,4-dimercapto-2,3-dihydroxy butane; and 2-mercaptoethanol. The latter is generally known simply as mercapto-ethanol. The first named compound has three optical isomers quite analogous to those of tartaric acid. The two isomers which are commercially available may also be names as, and are commonly known as, dithiothreitol, and dithioerythritol. Of these last two, the first is often known as "Cleland's Reagent"; while the second is often known as "Cleland's Other Reagent". We prefer dithiothreitol, conveniently abbreviated as DTT. Dithioerythritol may be abbreviated as DTE.

The prior art recognizes that the activators of the second class just given are CPK activators, but not that they are specifically CPK-MB activators as well, and thus utilizable in our inventive differential assay procedure. Exemplary of such prior art are the following:
 Clin.Chim.Acta 40 133 (1972) Kontinen et al.
 Clin.Chim.Acta 58 97–99 (1975) Miyada et al.
 Clinical Chem. 17 548–550 (1971) Bishop et al.
 Clinical CHem. 18 330–334 (1972) Dalal et al.
 Clincal Chem. 18 473–475 (1972) Warren.

We recognize a characteristic property of the CPK-MB thiol activators of the aforesaid second class which we believe plays a part in their effectiveness. This is a highly negative value of their oxidation-reduction potential, and specifically, lower than −0.31 volts, i.e., having an absolute magnitude greater than 0.31 volts, and of negative sign. Typical values are as follows;

| Activator | Oxidation-Reduction Potential, volts | Class |
|---|---|---|
| Thiodiglycolic acid | −0.14 | First |
| Cysteine | −0.21 | First |
| Glutathione | −0.25 | First |
| Mercaptoacetic acid | −0.30 | First |
| 2-mercaptoethanol | −0.32 | Second |
| DTE | −0.33 | Second |
| DTT | −0.33 | Second |

Additionally, we observe that the CPK-MB activator thiols, i.e., those of the second class which have been given above, not only have an oxidation-reduction potential of lower than −0.31 volts but are vicinal hydroxy thiols, that is, they bear mercapto and hydroxyl groups on adjoining carbon atoms.

A working example will now be given. An aqueous solution is prepared containing the following components in the concentrations given:

| | |
|---|---|
| Adenosine monophosphate (AMP) | $9.1 \times 10^{-3}$ molar |
| Creatine phosphate | $1.8 \times 10^{-2}$ molar |
| Adenosine diphosphate (ADP) | $1.1 \times 10^{-3}$ molar |
| Glucose-6-phosphate dehydrogenase(G-6-PDH) | 333 IU*/liter |
| Hexokinase (HK) | 1000 IU/liter |
| Glucose | $1.45 \times 10^{-2}$ molar |
| Piperazine-N,N'-bis(2-ethane sulfonic acid, sodium salt | $5 \times 10^{-2}$ molar |
| Glutathione | $8.7 \times 10^{-3}$ molar |
| Nicotinamide-adenine dinucleotide phosphate (NADP) | $5 \times 10^{-4}$ molar |
| The pH of the solution is 6.8. | |

*IU is International Units.

In this procedure, which is only one of many which may be used, all based on reaction [1] set forth above, reaction [1] proceeds from right to left, and is followed by:

$$\text{ATP} + \text{gluclose} \xrightarrow{\text{HK}} \text{G-6-P} + \text{ADP} \quad [2]$$

and:

$$\text{G-6-P} + \text{NADP} \xrightarrow{\text{G-6-PDH}} \text{NADPH} + \text{6-phosphogluconate.} \quad [3]$$

The NADPH (reduced NADP) absorbs light at 340 nm, and thus is a convenient measure of the CPK activity of the assay sample. The utility of the NADP-NADPH reaction generally is described in the Richterich text already cited; and the procedure set forth above is described in papers by Rao et al., *Clinical Research* 22 687A (1974), and ibid 23 203A (1975), and represents a modification of the method of Rosalki, *Proc. Assoc. Clin. Biochem.* 4 23 (1966) and *J. Lab. Clin. Med.* 69 (1967), all of which are hereby included herein by reference.

As will be clear from the foregoing disclosure, the test solution just given contains a CPK activator of the first group, namely, glutathione. Accordingly, when mixed with serum it will serve to measure essentially the CPK-MM concentration. This is done by bringing 3.0 ml of the test solution to preferably 30° C. (although the reaction proceeds well over the range 22° C. to 37° C.), adding 50 μ of serum or like fluid to be assayed, monitoring the absorbance until the reaction becomes linear, usually about five minutes, and determining ΔA/minute ($\Delta A_T$), where A is the absorbance. Normal sera can be used to establish the factors needed for conversion of the readings to absolute values, as will be readily understood by those skilled in the art, and indeed are set forth in the Rao et al. and Rosalki papers cited above. Specifically, for this example, for a one centimeter light path and 30° C., CPK in IU/ml is $\Delta A_T \times 9800$.

The entire operation is repeated after having first added an activator of the second class, namely, 1,4-dimercapto-2,3-dihydroxy butane or mercaptoethanol, or indeed any mixture of any of these, to the serum, and then proceeding as in the CPK/MM determination as already described. The presence of an activator of the first class, such as glutathione in the working example, does not interfere, so that the same test solution may be used instead of preparing a separate one not containing glutathione or the like. The CPK value then determined includes both the MM and MB isozymes, so that the CPK/MB value sought, and provided by the invention, is obtained by simply subtracting the value found without the second-class activator from that found when the latter is included.

For reliable results we have found that the activator of the second class should be premixed with the serum and at least a minute or two be allowed to elapse before proceeding with the rest of the assay. Such premixing is not necessary for the CPK-MM determination in which an activator of the first class is included in the procedure. In that case, it may be premixed if desired or simply be present in the test solution. Thus in either case it is included.

Coming back to our specific example, then, we mix 1 milliliter of the serum with 10 microliters of one molar aqueous DDT and mix by gentle inversion. 50 μl of this so-treated serum is then used for the CPK assay as already described. The values obtained from these two sub-procedures are then merely subtracted. The difference represents CPK/MB.

As already mentioned, our invention is applicable quite generally, whenever the creatine:ATP/ADP conversion is involved, in either direction. By way of an illustrative second specific example, we may employ our thiol of the second class in the procedure given in detail in the paper by Wiesmann et al., *Enzymologica biologica et clinica* 7 266 (1966), which paper is hereby included herein by reference.

In this procedure of Wiesmann et al., reaction [1] proceeds from left to right; the activator of the first class is cysteine; and an alternative enzyme system is used, resulting in the dehydrogenation of NADPH, so that the absorbance, measured at 366 nm, decreases.

For this second example of our invention, the procedure set forth in that paper is carried out, first, as given therein, using cysteine, and second, after pretreatment of the serum with an activator of the second class, such as mercaptoethanol or DTE or DTT, for example, added at the same concentration used in the first working example hereinabove. The difference in the two CPK values found corresponds to the CPK/MB present in the serum sample.

The relative proportions of serum and second-class activator are variable over a wide range. The same concentrations may be used as taught in the literature for thiol activators generally. We prefer a range of about 0.002 to 0.05 molar, and particularly the 0.01 molar concentration of thiol activator in the serum as indicated in the examples set forth above. A 0.01 molar concentration is, of course, 0.01 gram moles of solute per liter.

While our invention has been described with the aid of numerous specific examples, it will be recognized by those skilled in the art that many variations are possible without departing from the spirit and scope of the invention.

Having described the invention, we claim:

1. A process for determining the concentration of CPK-MB isoenzyme in a fluid to be tested comprising the steps of first determining the CPK activity in said fluid by use of the creatine: ATP/ADP conversion wherein said CPK has been activated by the inclusion in said fluid in the course of said activity determination of an activating thiol other than 1,4-dimercapto-2,3-dihydroxy butane and mercaptoethanol; separately determining a like activity subsequent to the addition to said fluid prior to said activity testing of a CPK-MB activator selected from the class consisting of 1,4-dimercapto-2,3-dihydroxy butane and mercaptoethanol and mixtures thereof; and determining said CPK-MB level as the arithmetic difference between the activities obtained in the two sub-procedures.

2. A process in accordance with claim 1 wherein said CPK-MB activator is the DTT isomer of said 1,4-dimercapto-2,3-dihydroxy butane.

3. A process for determining the concentration of CPK-MB isoenzyme in a fluid to be tested comprising the steps of first determining the CPK activity in said fluid by use of the creatine:ATP/ADP conversion wherein said CPK has been activated by the inclusion in said fluid in the course of said activity determination of a first activating thiol having an oxidation-reduction potential of higher than $-0.31$ volts; separately determining a like activity subsequent to the addition of said fluid prior to said activity testing of a second activating thiol having an oxidation-reduction potential of lower than $-0.31$ volts; and determining the CPK-MB level as the arithmetic difference between the activities obtained in the two sub-procedures.

4. A process in accordance with claim 3 wherein said second thiol is a vicinal hydroxy thiol.

5. A process in accordance with claim 1 wherein said fluid is serum.

6. A process in accordance with claim 2 wherein said fluid is serum.

7. A process in accordance with claim 3 wherein said fluid is serum.

8. A process in accordance with claim 4 wherein said fluid is serum.

9. A process in accordance with claim 5 wherein said fluid is serum.

* * * * *